United States Patent [19]
Okado et al.

[11] Patent Number: 6,043,051
[45] Date of Patent: *Mar. 28, 2000

[54] YEAST PROMOTER

[75] Inventors: Takashi Okado, Kyoto; Kazutoh Takesako, Otsu; Ikunoshin Kato, Uji, all of Japan

[73] Assignee: Takara Shuzo Co., Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/945,994

[22] PCT Filed: May 27, 1996

[86] PCT No.: PCT/JP96/01415

§ 371 Date: Nov. 6, 1997

§ 102(e) Date: Nov. 6, 1997

[87] PCT Pub. No.: WO96/38572

PCT Pub. Date: Dec. 5, 1996

[30] Foreign Application Priority Data

May 30, 1995 [JP] Japan ...................................... 7-154094

[51] Int. Cl.[7] ........................... C12P 21/00; C12N 15/63; C12N 1/15; C12N 15/31
[52] U.S. Cl. .................. 435/69.1; 435/320.1; 435/254.2; 536/23.1; 536/24.1; 536/24.5
[58] Field of Search ............................... 435/69.1, 254.2, 435/320.1; 536/23.1, 24.1, 24.5

[56] References Cited

FOREIGN PATENT DOCUMENTS

| | | |
|---|---|---|
| 9463129 | 12/1994 | Australia . |
| 0 352 092 | 1/1990 | European Pat. Off. . |
| 0 443 719 | 8/1991 | European Pat. Off. . |
| 0 581 429 | 2/1994 | European Pat. Off. . |
| 4-088988 | 3/1992 | Japan . |
| 5-279384 | 10/1993 | Japan . |
| 7-313172 | 12/1995 | Japan . |

OTHER PUBLICATIONS

F. Sherman, "Getting Started with Yeast", Method in Enzymology, vol. 194, pp. 1–21, 1991.

K. Takesako et al., "Aureobasidins, New Antifungal Antibiotics Taxonomy, Fermentation, Isolation, and Properties", Journal of Antibiotics, vol. 44, No. 9, pp. 919–924, 1991.

K. Ikai et al., "Structure of Aureobasidin A", The Journal of Antibiotics, vol. 44, No. 9, pp. 925–933, 1991.

K. Ikai et al. "Structures of Aureobasidins B to R", The Journal of Antibiotics, vol. 44, No. 11, pp. 1187–1198, 1991.

E. Balzi et al., "The Multidrug Resistance Gene PDR1 from *Saccharomyces cerevisiae*", The Journal of Biological Chemistry, vol. 262, No. 35, pp. 16871–16879, 1987.

*Primary Examiner*—John S. Brusca
*Attorney, Agent, or Firm*—Wenderoth, Lind & Ponack, L.L.P.

[57] ABSTRACT

This invention offers a promoter derived from a yeast which can be used in a complete nutrient medium and is transcriptionally controllable by a PDR1 gene product. Thus, this invention offers a DNA which is represented by SEQ ID NO:1 in the Sequence Listing or a part thereof and has a promoter activity in yeast; a DNA which can be transcriptionally controllable by a PDR1 gene product and has the above-mentioned promoter activity; and a DNA which is hybridizable to the above-mentioned DNA and has a promoter activity in yeast.

10 Claims, 1 Drawing Sheet

YEAST PROMOTER

TECHNICAL FIELD OF THE INVENTION

The present invention relates to a transcriptionally controllable promoter, derived from yeast, useful in molecular bioengineering for the manufacture of useful proteins, metabolites, etc. employing a gene recombinant DNA technique and also to a DNA where said promoter is linked to a heterologous gene in an expressible manner as well as to a vector containing said DNA. The present invention further relates to a method for the manufacture of protein using a vector containing a DNA obtained by linking a nucleic acid coding for the protein downstream of said promoter in an expressible manner.

PRIOR ART

In order to produce a protein which is useful as pharmaceuticals, food, etc. in a genetic engineering manner, its production in yeast using the yeast as a host has been widely conducted. A technique of introducing a heterologous gene into a yeast of the genus Saccharomyces (especially, Saccharomyces cerevisiae; hereinafter simply referred to as S. cerevisiae) for the production of the corresponding heterologous protein has been known. When the heterologous gene (including genomic DNA and cDNA) is expressed in S. cerevisiae cells, it is necessary to give an promoter expressible in the yeast upstream thereof. Examples of the promoter for S. cerevisiae which has been known so far are a promoter of alcohol dehydrogenase 1 (ADH 1) gene or a promoter of 3-phosphoglycerate kinase (PGK) gene known to show a strong expression; GAL1 and GAL10 promoter where a transcription is induced in a galactose medium; and PHO5 promoter where a transcription is induced in a medium having a low concentration of inorganic phosphate. It is desirable that a promoter is capable of conducting a transcriptional control and resulting in a far higher expressi on.

For a large-scale production of a heterologous protein by of yeast, it is preferred that a promoter not only shows a strong expression but also is capable of conducting a transcriptional control. It has been known that, in a synthetic minimum medium, a doubling time of a haploid strain of yeast is about 140 minutes while, in a complete nutrient medium, the time is as quick as about 90 minutes [Methods in Enzymology, 194, 15 (1991)]. Thus, as a condition for culturing the yeast to produce a heterologous protein, a complete nutrient medium abundant in nutrition is preferred since it accelerates the proliferating rate of the cells and can keep a high cell density. However, promoters capable of inducing a transcription which have been known up to now employ a medium wherein galactose is used as a carbon source or a medium having a low concentration of phosphate. Therefore, they are not preferred in terms of a cell proliferation for an purpose of a large-scale production of a heterologous protein.

OBJECTS OF THE INVENTION

An object of the present invention is to offer a nucleotide sequence of a promoter derived from a yeast which is capable of conducting a transcriptional control by a PDR1 gene product, and which can be used in a complete nutrient medium so that the above-mentioned problems have been solved.

SUMMARY OF THE INVENTION

The present inventors have found that expression of a gene related to the sensitivity to aureobasidin obtained from an aureobasidin-sensitive cells (a wild-type strain) increase when the aureobasidin-sensitive cells are subjected to a treatment such as a mutagenization to make them aureobasidin-resistant and have considered in offering a promoter which participates in said gene expression.

As a result of an intensive investigation, the present inventors have cloned a promoter which participates in the above gene expression from a genomic DNA of a mutant which is made aureobasidin-resistant and have determined the nucleotide sequence. To our surprise, when further investigation has been conducted, the present inventors have found that the transcriptional activity of said promoter is controlled by a gene product of a PDR1 gene of a pleiotropic drug resistance gene whereupon the present invention has been achieved.

The present invention will be summarized to be as follows. Thus, the first invention of the present invention relates to a promoter which is characterized in that it is a DNA represented by SEQ ID NO:1 in the Sequence Listing or a part thereof and having a promoter activity in yeast. The second invention relates to a DNA of the first invention wherein it is capable of conducting a transcriptional control by a PDR1 gene product. The third invention relates to a DNA which is characterized in being hybridizable to the DNA of the first invention and in having a promoter activity in yeast. The fourth invention relates to a DNA which is characterized in linking a heterologous gene to a DNA of any of the first to the third inventions in an expressible manner. The fifth invention relates to a vector which is characterized in containing a DNA of any of the first to the fourth inventions. The sixth invention relates to a yeast which is characterized in that the DNA of the fourth invention is introduced into the yeast or that the yeast is transformed by a vector of the fifth invention. The seventh invention relates to a method for the manufacture of a protein which is characterized in the use of a yeast transformed by a vector containing a DNA which is obtained by linking a nucleic acid encoding a protein in an expressible manner downstream of a DNA of any of the first to the third inventions.

DETAILED DESCRIPTION OF THE INVENTION

The term "promoter" used in the present specification is such a one, upstream to the transcriptional initiation point (+1), that contains a domain of TATA box or similar thereto having a function of initiating the transcription by an RNA polymerase from a precise position and that may contain an upstream activating sequence (UAS) and a domain which is necessary for associating with a protein other than the RNA polymerase for control of an expression.

The term "promoter activity" used in the present specification is such a one that shows an ability and a function of producing a gene product of a heterologous gene in or out of the host cell when the heterologous gene links to a down stream of the promoter in an expressible manner and that, introduced into a host (yeast).

Usually, a gene (a reporter gene) encoding a protein which can be easily quantitatively examined is linked to a down stream of a promoter in an expressible manner and introduced into a host, and then the expression of such a protein is measured whereby the presence/absence and the potency of the promoter are represented as an activity of the promoter. When the heterologous gene is linked down stream of the promoter in an expressible manner, introduced into the host and an expression of the gene product is confirmed in or out of host, said promoter has a promoter activity in the host into which the promoter is introduced.

The term "PDR1 gene product" used in the present specification includes a gene product which is obtained directly from a PDR1 gene and also a gene product which is obtained from a PDR1 gene modified by means of at least one of substitution, insertion and deletion of a part of nucleotide by a natural mutagenesis or by a site-specific mutagenesis.

The term "heterologous gene" used in the present specification is a gene which is heterologous (i.e., foreign) to a host (yeast) and is, for example, nonfungus gene, modified gene, gene of a different fungus species, self-cloned gene, etc. The heterologous gene includes a gene coding for a protein which is expressible in yeast, antisense DNA or antisense RNA of gene derived from yeast, a gene coding for a transcriptional factor derived from a yeast, a nucleotide sequence of a binding site of the factor, a decoy having similar sequence thereto, and a ribozyme which cleaves an mRNA derived from the yeast, etc.

An example of the gene coding for the protein which is expressible in yeast is that which is derived from yeast but the present invention is not limited thereto but any gene which is derived from microorganisms (such as bacteria, Actinomycetes, filamentous fungi, Ascomycetes and Basidiomycetes) and from living organisms (such as plants, insects and animals) is included in the heterologous gene of the present specification so far as the gene is expressible in yeast.

In addition, any protein which is produced by the above-mentioned heterologous gene will be called a heterologous protein.

The term "decoy" used in the present specification is a gene coding for the transcriptional factor derived from the yeast, a DNA having a sequence of the binding site of a transcriptional factor, and a DNA having a similar sequence thereto. When it is introduced into the yeast as a "decoy bird", the function of the transcription factor can be suppressed.

The term "ribozyme" used in the present specification is that which cleaves an mRNA of a specific protein and inhibits the translation of such a specific protein. Ribozyme can be designed from a gene sequence coding for a specific protein. With regard to a ribozyme of a hammerhead type, a method mentioned in FEBS Letter, 228, 228–230 (1988) may be used. Foreover, not only the hammerhead ribozyme, but also any ribozyme such as a hairpin ribozyme and a delta ribozyme in regardless to the type of the ribozyme may be included in "ribozyme" of the present specification so far as it cleaves the mRNA of a specific protein and inhibits the translation of such a specific protein.

Aureobasidin [Japanese Laid-Open Patent Publications Hei-02/138,296, 03/022,995, 03/220,199, 05/279,384 and 06/065,291; Journal of Antibiotics, 44, (9), 919–924; ibid., 44, (9), 925–933; and ibid., 44, (11), 1187–1198 (1991)] is a cyclic depsipeptide obtained as a fermentation product of the strain Aureobasidium pullulans No. R106 (FERM BP-1938) and is entirely different from other antimycotics in terms of their structure. As shown in Tables 1 and 2 which will be given below, aureobasidin A which is a typical aureobasidin compound shows a very potent antimycotic activity on various yeasts of the genus Candida (such as C. albicans), Cryptococcus neoformans, Histoplasma capsulatum, Blastomyces dermatidis and fungi of the genus Asperaillus (Japanese Laid-Open Patent Publication Hei-02/138,296) but has a very weak toxicity. Accordingly, this is an antimycotic agent having an excellent selective toxicity.

Hereinafter, Candida, Cryptococcus and Asperaillus will be abbreviated as C., Cr. and A., respectively. In the following Tables 1 and 2, the term "MIC" stands for a minimum inhibitory concentration ($\mu$g/ml) of aureobasidin to various fungi.

TABLE 1

| Tested Microorganisms | TIMM Number | MIC ($\mu$g/ml) |
|---|---|---|
| C. albicans | 0136 | ≦0.04 |
| C. albicans var. stellatoidea | 1308 | ≦0.04 |
| C. tropicalis | 0312 | 0.08 |
| C. kefyr | 0298 | 0.16 |
| C. parapsilosis | 0287 | 0.16 |
| C. krusei | 0270 | ≦0.04 |
| C. guilliermondii | 0257 | 0.08 |
| C. glabrata | 1062 | ≦0.04 |
| Cr. neoformans | 0354 | 0.63 |
| Cr. terreus | 0424 | 0.31 |
| Rhodotorula rubra | 0923 | 0.63 |
| A. fumigatus | 0063 | 20 |
| A. clavatus | 0056 | 0.16 |

TABLE 2

| Tested Microorganism | TIMM Number | MIC ($\mu$g/ml) |
|---|---|---|
| A. nidulans | 0112 | 0.16 |
| A. terreus | 0120 | 5 |
| Penicillium commune | 1331 | 1.25 |
| Trichophyton mentagrophytes | 1189 | 10 |
| Epidermophyton floccosum | 0431 | 2.5 |
| Fonsecaea pedrosoi | 0482 | 0.31 |
| Exophiala werneckii | 1334 | 1.25 |
| Cladosporium bantianum | 0343 | 0.63 |
| Histoplasma capsulatum | 0713 | 0.16 |
| Paracoccidioides brasiliensis | 0880 | 0.31 |
| Geotrichum candidum | 0694 | 0.63 |
| Blastomyces dermatitidis | 0126 | 0.31 |

As mentioned in the Japanese Laid-Open Patent Publication Hei-07/313,172, the present inventors have found that the fungi such as Schizosacchromyces pombe (hereinafter, abbreviated as Schizo. pombe) and S. cerevisiae are sensitive to aureobasidin.

TABLE 3

| Tested Microorganism | MIC ($\mu$g/ml) |
|---|---|
| Schizo. pombe | 0.08 |
| S. cerevisiae | 0.31 |

The present inventors have mutagenized a wild-type strain of Schizo. pombe, S. cerevisiae, etc. which are sensitive to aureobasidin to give resistant cells (resistant strain) and have succeeded in isolating a gene (a resistant gene) capable of conferring an aureobasidin resistance from the resistant strain and also in isolating a gene (a sensitive gene) capable of imparting the corresponding aureobasidin sensitivity from the wild-type strain. Furthermore, the present inventors have clarified the existence of a protein encoded by each of those genes. Moreover, the present inventors have constructed a replication vector wherein said gene is contained, and have succeeded in expressing the above-mentioned gene, the cells transformed by said vector. Still further, the present inventors have succeeded in finding a novel gene related to the aureobasidin sensitivity from other fungi which are sensitive to aureobasidin, using the DNA fragment of the above-mentioned gene as a probe.

Gene which is related to an aureobasidin sensitivity (aur) is a gene coding for a protein related to the aureobasidin sensitivity and includes a sensitive gene and a resistant gene.

For isolating the gene which is related to an aureobasidin sensitivity, a resistant strain is first induced from aureobasidin-sensitive cells (a wild-type strain) by means of a mutagenesis, a DNA library is prepared from a chromosomal DNA or cDNA of this resistant stain and then a gene which is capable of conferring a resistance (a resistant gene) is cloned from this library. When a DNA library of the wild-type strain is prepared and then a DNA molecule being hybridizable with the resistant gene is isolated from this library, it is possible to isolate a sensitive gene.

Examples of the mutagenesis are a method of treating with a chemical agent such as ethyl methanesulfonate (EMS) or N-methyl- N'-nitro-N-nitrosoguanidine (NTG) and a method treating with ultraviolet or other radiations. The cell that has acquired the resistance can be screened by culturing the mutagenized cells in a nutritional medium containing an appropriate concentration of aureobasidin under appropriate conditions. The resulting resistant strain may vary depending upon the method and conditions for the mutagenesis employed.

The present invention will now be specifically illustrated using *S. cerevisiae* DKD8D strain (mating type: a; genetic type: leu2-3.112, trp1, ura3-52, his4) as an example of a strain of a wild type.

*S. cerevisiae* DKD8D strain which is sensitive to aureobasidin is subjected to a mutagenesis using EMS and *S. cerevisiae* AL33-18C strain which is not resistant to multiple drugs but is specifically resistant to aureobasidin is isolated from the resulting mutants.

Said strain has been named and designated as *Saccharomyces cerevisiae* AL33-18C. This strain has been deposited at the National Institute of Bioscience and Human Technology, Agency of Industrial Science and Technology, MITI (located at 1-3, Higashi-1-chome, Tsukuba City, Ibaragi Prefecture 305, Japan) under the accession number FERM P-14920 and transferred to a deposition according to a Budapest Treaty at the same organization being deposited under the accession number FERM BP-5529.

Then the expression of the gene related to an aureobasidin sensitivity of *S. cerevisiae* DKD8D strain and of *S. cerevisiae* AL33-18C strain are confirmed. For confirming the expression, total RNA from each of those two strains is extracted.

When the total RNA is subjected to a northern hybridization using a scaur2 gene mentioned, for example, in the Japanese Laid-Open Patent Publication Hei-07/313,172 as a probe, expression of the scaur2 gene which is a gene related to an aureobasidin sensitivity can be confirmed.

Figure 1:
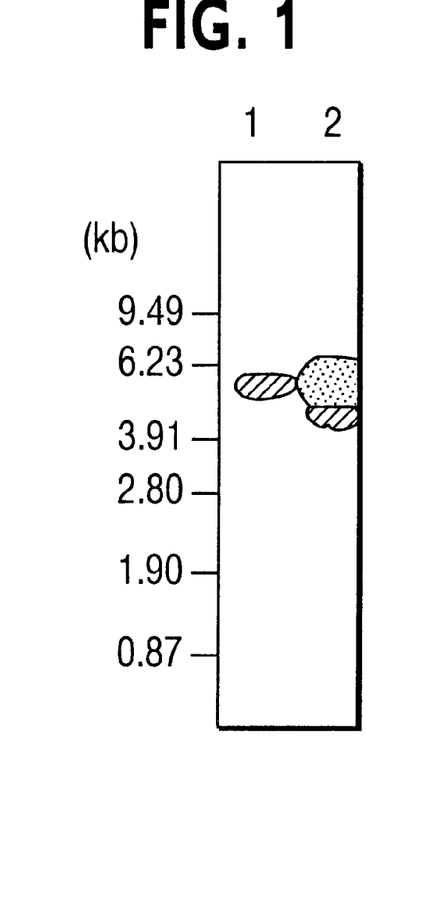
FIG. 1 shows the result of northern hybridization of a wild-type strain and an aureobasidin-resistant strain of S. cerevisiae using the scaur2 gene as a probe.

The result is given in FIG. 1. As shown in FIG. 1, expression of the scaur2 gene was very high in *S. cerevisiae* AL33-18C strain which was a strain resistant to aureobasidin. The scaur2 gene used as a probe is contained in a plasmid pSCAR2. *E. coli* HB101 which possesses said plasmid pSCAR2 has been named and designated as *Escherichia coli* HB101/pSCAR2 and deposited at the National Institute of Bioscience and Human Technology, Agency of Industrial Science and Technology, MITI under the accession number FERM BP-4484.

Figure 2:
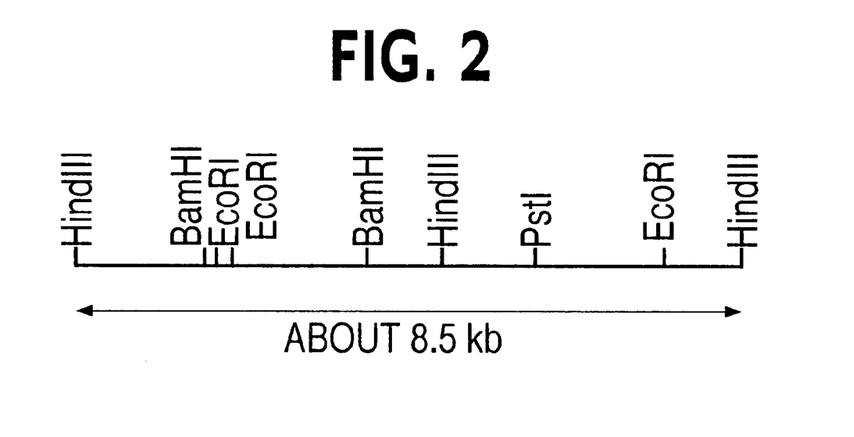
FIG. 2 shows a restriction enzyme map of the scaur2 gene.

Then a cloning of a promoter, which is thought to be present upstream of the scaur2 gene, showing a very high expression is attempted. In order to clone the promoter, a cloning of the scaur2 gene which is a gene related to an aureobasidin sensitivity is first performed from *S. cerevisiae* AL33-18C strain. In the cloning of the scaur2 gene, a method mentioned in the Japanese Laid-Open Patent Publication Hei-07/313,172 may be used. For example, a genomic DNA is prepared from *S. cerevisiae* AL33-18C strain and a genomic library is prepared. After that, said genomic library is screened by a hybridization using the scaur2 gene mentioned in the above-mentioned Japanese Laid-Open Patent Publication Hei-07/313,172 as a probe whereby the scaur2 gene of *S. cerevisiae* AL33-18C strain can be obtained. A restriction enzyme map of DNA fragment containing said scaur2 gene is shown in FIG. 2. In order to confirm whether said scaur2 gene is a gene related to an aureobasidin sensitivity, the nucleotide sequence of scaur2 gene of *S. cerevisiae* AL33-18C strain is determined and compared with the nucleotide sequence of scaur2 gene mentioned in the Japanese Laid-Open Patent Publication Hei-07/313,172 and also with an amino acid sequence of a protein coded by the scaur2 gene presumed from the nucleotide sequence. The nucleotide sequence of the domain containing the protein coding region of the scaur2 gene of *S. cerevisiae* AL33-18C strain is shown in SEQ ID NO:2 in the Sequence Listing while the amino acid sequence presumed from the nucleotide sequence of said gene is shown in SEQ ID NO:3 in the Sequence Listing.

As a result, it was confirmed that the scaur2 gene of *S. cerevisiae* AL33-18C strain was a gene related to an aureobasidin sensitivity. Then, a promoter which is thought to be located upstream of said scaur2 gene is cloned. For example, a DNA fragment containing said scaur2 gene is digested with an appropriate restriction enzyme to subclone the DNA fragment containing the region upstream of the scaur2 gene whereupon the nucleotide sequence is determined. Among said nucleotide sequence, that which is located upstream of the scaur2 gene is shown in SEQ ID NO:4. Only the region upstream to the scaur2 gene can be obtained by a PCR or the like too. For example, a primer (SEQ ID NO:5) corresponding to the upstream of the above-mentioned DNA fragment is designed from the SEQ ID NO:4 while a primer (SEQ ID NO:6) corresponding to the upstream of the scaur2 gene was designed from the SEQ ID NO:2 and then a PCR is conducted using those primers whereupon a DNA fragment containing a promoter can be prepared. The nucleotide sequence of said DNA fragment is shown in SEQ ID NO:1 in the Sequence Listing.

Then, in order to confirm whether said DNA fragment functions as a promoter, said DNA fragment is integrated into an appropriate vector to prepare a recombinant vector wherein a heterologous gene is connected therewith downstream of the same direction as said DNA fragment. And a terminator is connected therewith downstream of the heterologous gene at the same direction. With respect to the terminator, anything which has been known or which will be present downstream of the scaur2 gene may be used. In order to obtain a terminator which is downstream of the scaur2 gene, a PCR is conducted using a primer (SEQ ID NO:7) corresponding to downstream of the scaur2 gene and another primer corresponding to a vector sequence of the recombinant plasmid integrated with a DNA fragment containing the scaur2 gene [when a vector is pUC119 for example, an M13 primer M3 (manufactured by Takara Shuzo) may be used] whereupon a DNA fragment containing a terminator can be obtained. The nucleotide sequence of the terminator is shown in SEQ ID NO:8 in the Sequence Listing. The resulting recombinant plasmid is transformed into yeast or the like to check an expression of a heterologous gene or a heterologous protein whereby it can be confirmed whether the said DNA fragment functions as a promoter or not. For example, β-galactosidase gene [Methods in Enzymology, 100, 293–308 (1983)] is used as a heterologous gene and connected to a downstream of the above-mentioned DNA fragment to the same direction to produce a recombinant vector. Said recombinant vector is transformed into yeast, the resulting recombinant cell is cultured on a medium containing 5-bromo-4-chloro-3-indolyl-β-D-galactoside (X-gal) and an observation is conducted whether color of the formed colonies change blue by the expressing galactosidase whereby it can be confirmed whether said DNA fragment has a promoter activity.

As a result, it has been now clarified that the DNA fragment containing the promoter of the present invention has a promoter activity.

Then, in order to confirm whether the apparent difference in expression of the scaur2 gene between the above-mentioned *S. cerevisiae* DKD8D strain and *S. cerevisiae* AL33-18C strain is due to the activity of the promoter contained in the above-mentioned DNA fragment, the above-mentioned recombinant vector used for the confirmation of the promoter activity is transformed into each of the wild-type strain and the aureobasidin-resistant strain. Examples of the wild-type strain applicable are *S. cerevisiae* DKD8D strain, *S. cerevisiae* SH3328 strain (mating type: α; genetic type: ura3-52, his4, thr4, leu2-3.112), etc. while an example of the aureobasidin-resistant strain is *S. cerevisiae* AL33-18C strain. The resulting recombinant cells are cultured and the growing cell is collected and homogenized. A galactosidase activity of the crushed cell homogenate is measured using O-nitrophenyl-β-D-galactoside (ONPG) as a substrate (Experiments in Molecular Biology, page 352–355, Cold Spring Harbor Laboratory, 1972) whereby the expression amount of the β-galactosidase gene can be measured as an enzymatic activity of β-galactosidase. The result is that, as well as in the result where the expression of the scaur2 gene are compared, the recombinant cell of *S. cerevisiae* AL33-18C strain transformed with the recombinant vector showed very higher activity. Accordingly, it is now clear that there is transcriptionally regulatory factor which induces a high expression of the promoter of the present invention.

Then, in order to confirm what this factor for a transcriptional regulation is, genetic analysis of *S. cerevisiae* AL33-18C strain was performed. As a result thereof, it was now clarified that a mutation took place in a PDR1 gene among pleiotropic drug resistance genes which has been known as a factor for transcriptional regulation [Journal of Biological Chemistry, 262, (35), 16871–16879 (1987)], that the transcription of the promoter of the present invention was regulated by said PDRI gene product, and that the promoter of the present invention was capable of conducting a transcriptional regulation by the PDR1 gene product.

In accordance with the present invention, it is now possible that, by the use of a promoter of the present invention, expression of a gene connected to an expressible position downstream of said promoter is controlled by the PDR1 gene product and said promoter is useful in the manufacture of a useful recombinant protein and the like. In addition, when yeast is used as a host for a transformation, the promoter of the present invention is useful for a large-scale production of a useful recombinant protein, because the recombinant cell is capable to culture in a complete nutrient medium having a high nutrition wherein the proliferating rate of the cell is high and a high cell concentration can be maintained.

The promoter of the present invention can be prepared from *S. cerevisiae* AL33-18C strain. By using nucleotide sequence containing the promoter of the present invention, it is now possible to prepare a promoter which is capable of hybridizing to said nucleotide sequence, which has the same properties as the promoter of the present invention, and which is useful for the manufacture of a recombinant protein. Said promoter is covered by the present invention as well.

With respect to a method for the preparation of the desired promoter by means of a hybridization, the following method may, for example, be applied. Thus, at first, the chromosomal DNA obtained from the aimed gene source is connected with a plasmid or a phage vector to introduce into a host according to a conventional method whereupon a DNA library is prepared. The library is cultured on plates, the grown colonies or plaques are taken up onto a membrane of nitrocellulose or nylon and a denaturation treatment is conducted so that the DNA from colonies on plaques is fixed to the membrane. The membrane is kept to warm in a solution containing a probe which was previously labeled with $^{32}P$ or the like (with regard to the probe used here, that which has a nucleotide sequence of SEQ ID NO:1 and NO:4 in the Sequence Listing or a part thereof may be used) whereby a hybrid is formed between the DNA and the probe on the membrane. Thus, for example, a membrane in which the DNA is fixed is subjected to a hybridization with the probe at 65° C. for 20 hours in a solution containing 6×SSC, 1% sodium laurylsulfate, 100 μg/ml of salmon sperm DNA and 5×Denhardt's solution (containing each 0.1% of bovine serum albumin, polyvinylpyrolidone and Ficoll). After the hybridization, nonspecific adsorption is washed out and a clonal plasmid or phage forming a hybrid with the probe is identified by means of an autoradiography or the like. Such an operation is repeated until the hybridized clone becomes a single one. The aimed promoter is found to be inserted into the clonal plasmid or phage prepared as such.

Nucleotide sequence of the resulting DNA is determined, for example, by the following manner so that it is confirmed whether the resulting DNA is an aimed promoter or not.

Thus, in the case of a clonal plasmid obtained by a hybridization, a recombinant *E. coli* is cultured using a test tube or the like and a plasmid is extracted from the recombinant by a conventional means. This is cleaved by a restriction enzyme, the inserted fragment is taken out and subcloned to M13 phage vector or the like and the nucleotide sequence is determined by a dideoxy method. When the recombinant is a phage, fundamentally same steps may be conducted for determining the nucleotide sequence. The fundamental experimental method from the culturing to the determination of the nucleotide sequence is mentioned, for example, in Molecular Cloning, A Laboratory Manual, by T. Maniatis, et al, Cold Spring Harbor Laboratory, 1982.

In order to confirm whether the resulting DNA is an aimed promoter or not, the determined nucleotide sequence is compared with the nucleotide sequence of the promoter of the present invention and with that mentioned in SEQ ID NO:1 in the Sequence Listing whereby its genetic structure is elucidated.

When the resulting DNA does not contain all region of the promoter, the region which is deficient in the resulting DNA is amplified using a synthetic DNA prepared based upon the resulting DNA by PCR or a DNA library is further screened using a fragment of the DNA as a probe whereby the nucleotide sequence of entire region of the promoter which hybridizes with the promoter of the present invention can be determined.

For example, it is possible to obtain an aimed promoter using *S. cerevisiae* L22-8B strain which is resistant to aureobasidin and is mentioned in the Japanese Laid-Open Patent Publication Hei-07/313,172 as a gene source.

Further, based upon the nucleotide sequence of the promoter of the present invention, a site-specific mutagenesis of the DNA containing said nucleotide sequence is conducted to modify a part of said nucleotide sequence by means of at least one of substitution, insertion and deletion of nucleotide whereby it is possible to modify the function of the promoter of the present invention and to afford a promoter which is similar to the promoter of the present invention. With respect to the site-specific mutagenesis, several methods such as a gapped duplex method [Methods in Enzymology, 154, 350–367 (1987)], a uracil DNA method [Methods in Enzymology, 154, 367–382 (1987)], a nitrite method [Proceedings of the National Academy of Sciences of the USA, 79, 7258–7262 (1982)] and a cassette mutation method [Gene, 34, 315–323 (1985)] have been known.

It is also possible that, based upon the nucleotide sequence of the promoter of the present invention, a DNA containing said nucleotide sequence or a part of it is linked to or substituted with a DNA of known promoter or a part of it to prepare a promoter of chimera [Proceedings of the National Academy of Sciences of the USA, 88, 7266–7270 (1991)] whereby, like the promoter of the present invention, a promoter which is capable of being transcribed by the PDR1 gene product can be obtained.

The promoter which is prepared as such is able to confirm whether the promoter functions in a cell by connecting various reporter genes at the position downstream thereof and by measuring the promoter activity by the same methods as in the case of the promoter of the present invention.

The promoter of the present invention and a promoter which is capable of hybridizing with said promoter and has the similar property as the promoter of the present invention has can be used as a recombinant vector by integrating with an appropriate vector either solely or jointly with a terminator. Examples of the vector which can be used are pYR type, pYC type, pYE type, pYI type, etc. in the case of a vector for yeast. One or more structural gene (s) can be integrated into said recombinant vector in an expressible direction. Further, it is preferred that the recombinant vector integrated with said structural gene contains a signal sequence which secretes the gene product expressed from said structural gene to the outside of the cells. With respect to the cell which is used for transformation of said recombinant vector and the recombinant vector wherein the structural gene is integrated, any cell may be used so far as it is a cell in which the promoter of the present invention or the promoter which is capable of hybridizing with said promoter and has the similar property as the promoter of the present invention has exhibits a promoter activity and its preferred example is yeast. With respect to a method for transforming said recombinant vector or the recombinant vector containing a structural gene into those cells, any of the known methods such as a protoplast method, a lithium acetate method, an electroporation method, etc. may be used.

Further, when both of said recombinant vector or the recombinant vector containing structural gene and the recombinant vector containing a PDR1 gene is integrated in such a manner that can be expressed in an appropriate vector are transformed into the same cell, it is possible to regulate the transcription of the promoter of the present invention or the promoter which is capable of hybridizing with said promoter and has the same property as the promoter of the present invention has.

Furthermore, when said recombinant vector or the recombinant vector into which the structural gene or the like is integrated is used for protein the synthesis in a cell-free system and a PDR1 gene product is added thereto from outside or it is put thereinto from the initial stage, it is possible to regulate the transcription from the promoter of the present invention or the promoter which is capable of hybridizing with said promoter and has the same property as the promoter of the present invention has and it is also possible to conduct a synthesis of a protein in a better mode than the protein synthesis in usual cases.

Now the present invention will be specifically illustrated by way of the following examples although the present invention is not limited thereto.

EXAMPLE 1

Isolation of aureobasidin-resistant mutant of *S. cerevisiae*.

About $1 \times 10^8$ cells of *S. cerevisiae* DKD8D strain (mating type: a; genotype: leu2-3.112, tripl, ura3-52, his4) exhibiting a sensitivity of 0.31 µg/ml to aureobasidin A were suspended in 1 ml of a phosphate buffer containing 0.9% of sodium chloride. Mutagenesis was performed with 3% (in terms of a final concentration) of EMS under the condition at 30° C. for 90 minutes. EMS was inactivated with 8 ml of 5% sodium thiosulfate and the treated cells were recovered by centrifugation (2,500 rpm for five minutes), washed with 6 ml of saline solution twice and suspended in 2 ml of a YPD medium (containing 2% of glucose, 1% of yeast extract and 2% of polypeptone). The suspension was kept at 30° C. for five hours with stirring, spread on a YPD plate (a YPD medium containing 1.5% of agar) containing 1.5 µg/ml of aureobasidin A and incubated at 30° C. for three to four days. The resistant mutant *S. cerevisiae* AL33-18C strain obtained as such was resistant even to 25 µg/ml of aureobasidin A and was presumed not to be resistant to many other chemicals but specifically resistant to aureobasidin.

Said strain has been named and designated as *Saccharomyces cerevisiae* AL33-18C and deposited at the National Institute of Bioscience and Human Technology, Agency of Industrial Science and Technology, MITI (located at 1-3, Higashi-1-chome, Tsukuba City, Ibaragi Prefecture 305, Japan) on May 11, 1995 under the accession number FERM P-14920 and also at the same organization (being transferred to an international deposition on May 9, 1996) under the accession number FERM BP-5529.

EXAMPLE 2

Expression of scaur2 gene in *S. cerevisiae* DKD8D strain and *S. cerevisiae* AL33-18C strain.

Total RNA was extracted and purified from *S. cerevisiae* DKD8D strain which is a wild-type strain of *S. cerevisiae* and also from *S. cerevisiae* AL33-18C strain which is an aureobasidin resistant strain prepared in Example 1 by a method of R. Jensen et al [Proceedings of the National Academy of Sciences of the USA, 80, 3035–3039 (1983)]. Then poly(A)RNA was purified using an oligotex-dT30 (manufactured by Takara Shuzo). Purified poly (A) RNA (2.5 µg) was separated by means of an electrophoresis using 1.2% agarose gel containing formaldehyde and then fixed after transferring onto a nylon membrane (Hybond-N;

manufactured by Amersham). As a probe for confirming the expression of scaur2 gene, pSCAR2 was prepared from E.coli HB101/pSCAR2 (FERM BP-4484) possessing a plasmid pSCAR2 containing the scaur2 gene derived from S. cerevisiae L22-8B strain which was resistant to aureobasidin mentioned in the Japanese Laid-Open Patent Publication Hei-07/313,172 and then subjected to a double digestion with HindIII (manufactured by Takara Shuzo) and PstI (manufactured by Takara Shuzo) followed by subjecting to an agarose gel electrophoresis to recover and purify a HindIII-PstI fragment (1.2 kbp) of the scaur2 gene. Said DNA fragment was labeled with ($\alpha$-$^{32}$P)dCTP and the labeled one was used as a probe for conducting a hybridization with the above-mentioned fixed poly(A)RNA. The result is given in FIG. 1. Thus, FIG. 1 is an autoradiograph of the result when the mRNA obtained from the wild-type strain or from the resistant strain was subjected to an electrophoresis with 1.2% of agarose gel containing formaldehyde followed by subjecting to northern hybridization. In the figure, lanes 1 and 2 show the mRNA obtained from the wild-type strain and from the resisting strain, respectively. The result shows that, expression of scaur2 mRNA in S. cerevisiae AL33-18C strain was 50-fold or more higher than that in S. cerevisiae DKD8D strain.

EXAMPLE 3

Cloning of promoter of the scaur2 gene.

(1) Cloning of the scaur2 gene.

In order to clone the promoter of scaur2 gene, the scaur2 gene was cloned from S. cerevisiae AL33-18C strain.

A genomic DNA was extracted and purified from S. cerevisiae AL33-18C strain resistant to aureobasidin obtained in Example 1 by a method of P. Philippsen et al [Methods in Enzymology, 1, 169–175 (1981)].

Purified genomic DNA (8 µg) was subjected to a partial digestion by HindIII 5 Unit at 37° C. for ten minutes, deproteinized with phenol-chloroform and precipitated with ethanol to give a partially digested DNA. This DNA was subjected to an electrophoresis using 0.8% agarose gel and DNA ranging in 3–15 kbp was extracted and purified. This DNA was ligated with a yeast-E. coli shuttle vector pWH5 (2µg) which was completely digested with HindIII [Plasmid, 15, 156–158 (1986)) using a DNA ligation kit (manufactured by Takara Shuzo) and then transformed to E. coli HB101 to prepare a genomic library. E. coli containing a genomic library was spread on an LB agar medium containing ampicillin and tetracycline and incubated overnight at 37° C. The resulting colonies were transferred onto a nylon membrane (Hybond-N) and subjected to a colony hybridization. As a probe, the DNA fragment of 8.5 kbp containing a scaur2 gene used in Example 2, mentioned in the Japanese Laid-Open Patent Publication Hei-07/313, 172 and labeled with ($\alpha$-$^{32}$P) dCTP using a random primer DNA labeling kit (manufactured by Takara Shuzo) was used. As a result of the screening of 2×10$^4$ colonies, several clones which hybridize with the probe was obtained. Those clones contained a DNA fragment of 8.5 kbp consisting of HindIII DNA fragments of 4.6 kbp and 3.9 kbp. From the restriction enzyme maps of those DNA fragments, it was found that it was scaur2 gene mentioned in the Japanese Laid-Open Patent Publication Hei-07/313,172. Said DNA fragment of 8.5 kbp is shown in FIG. 2.

The resulting DNA fragment of 8.5 kbp was subcloned into pUC118 (manufactured by Takara Shuzo) and then the DNA nucleotide sequence was determined (SEQ ID NO:2). Based on the nucleotide sequence of SEQ ID NO:2 in the Sequence Listing, the amino acid sequence represented by the SEQ ID NO:3 in the Sequence Listing was estimated.

Incidentally, said DNA fragment of 8.5 kbp was subcloned into a HindIII site of pUCll9 (manufactured by Takara Shuzo) and the plasmid was named pUscaur2 and E. coli HB101 possessing said pUscaur2 was named Escherichia coli HB101/pUscaur2.

(2) Cloning of promoter of scaur2 gene and determination of nucleotide sequence.

pUscaur2 prepared in Example 3-(1) was digested with a restriction enzyme BamHI (manufactured by Takara Shuzo), subjected to an electrophoresis with 0.8% agarose and a DNA fragment of about 2 kbp which was thought to contain a promoter therein was extracted and purified. Then, said DNA fragment was made into a form of blunt ends using a DNA blunting kit (manufactured by Takara Shuzo) and inserted into a SmaI site of pUC118. The resulting plasmid was used for determining the nucleotide sequence. Among the determined nucleotide sequence, that which was upstream of the scaur2 gene is shown in SEQ ID NO:4 in the Sequence Listing.

Then, in order to obtain only DNA fragment containing a promoter which was upstream of the scaur2 gene, a primer wherein HindIII recognition sequence was added to a 5'-terminal side of the nucleotide sequence corresponding to the upper region of the above DNA fragment from SEQ ID NO:4 in the Sequence Listing was designed. Nucleotide sequence of said primer is shown in SEQ ID NO:5 in the Sequence Listing. Next, a primer to which BamHI recognition sequence to the 5'-terminal side of the nucleotide sequence corresponding to the upstream region of the scaur2 gene from SEQ ID NO:2 in the Sequence Listing was designed. Nucleotide sequence of said primer is shown in SEQ ID NO:6 in the Sequence Listing. PCR was conducted using both primers with the plasmid pUscaur2 as a template. The product of the PCR was digested with HindIII and BamHI and subjected to an electrophoresis with 0.8% agarose gel whereupon a HindIII-BamHI DNA fragment of about 1.4 kbp obtained by the PCR was extracted and purified. Said DNA fragment was cloned to a HindIII-BamHI site of pUC119 to determine the nucleotide sequence. Among said nucleotide sequence, that which corresponds to pUscaur2 is shown as SEQ ID NO:1 in the Sequence Listing.

(3) Cloning of a terminator of scaur2 gene and determination of a nucleotide sequence.

In order to clone the DNA fragment containing a terminator downstream to the scaur2 gene, a primer to which SmaI recognition sequence was added to a 5'-terminal side of the nucleotide sequence corresponding to the downstream region of the scaur2 gene was designed. Nucleotide sequence of said primer is shown as SEQ ID NO:7 in the Sequence Listing.

PCR was conducted using said primer and M13 primer M3 (manufactured by Takara Shuzo) with pUscaur2 as a template. The product of the PCR was digested with SmaI (manufactured by Takara Shuzo) and subjected to an electrophoresis using 0.8% agarose gel whereupon an SmaI DNA fragment of about 1.1 kbp obtained by the PCR was extracted and purified. Said DNA fragment was cloned to the SmaI site of pUC119 to determine the nucleotide sequence. Among said nucleotide sequence, that which corresponds to pUscaur2 is shown as SEQ ID NO:8 in the Sequence Listing.

EXAMPLE 4

Measurement of the promoter activity.

(1) Construction of a plasmid where a β-galactosidase is introduced into a downstream of the promoter of the scaur2 gene.

The HindIII-BamHI DNA fragment (about 1.4 kbp) containing the promoter obtained in Example 3-(2) was inserted into a HindIII-BamHI site of the pUC119 and then the SmaI DNA fragment (about 1.1 kbp) containing the terminator obtained in Example 3-(3) was inserted in the same direction as the DNA fragment containing the promoter whereby a plasmid pUscaur2P-T was prepared.

Next, a β-galactosidase gene was inserted into the pUscaur2P-T according to the following method. Thus, with respect to the β-galactosidase (lacZ) gene, a plasmid pMC1871 [Methods in Enzymology, 100, 293–308 (1983)] was cleaved by BamHI and the desired DNA fragment of about 3.1 kbp was separated by means of an electrophoresis with 0.8% agarose gel whereby it was recovered and purified. This DNA fragment of 3.1 kbp was inserted into a BamHI site of pUscaur2P-T in the same direction as the promoter-containing DNA fragment described above to give a plasmid pUAR2LZ having the β-galactosidase gene downstream to the promoter.

(2) Construction of a yeast replication pYC plasmid wherein a β-galactosidase gene is introduced downstream of the promoter of scaur2.

pUAR2LZ was digested with HindIII and a DNA fragment of about 5.4 kbp containing the promoter of scaur2 gene, the terminator of scaur2 gene and the β-galactosidase gene was separated by an electrophoresis with 0.8% agarose gel and it was recovered and purified. The DNA fragment of 5.4 kbp blunted by a DNA blunting kit was connected to a blunted BamHI-EcoRiI site of pYEUra3 (manufactured by Clontech) which was a pYC vector. The plasmid which was prepared as such was named pYCAR2LZ.

(3) Expression of a β-galactosidase gene from the promoter of scaur2 gene in wide-type strain and an aureobasidin-resistant strain.

The pYCAR2LZ obtained in Example 4-(2) was transformed by a lithium acetate method to S. cerevisiae SH3328 strain (mating type: α; genotype: ura3-52, his4, thr4, leu2-3.112) (wide type) and to S. cerevisiae AL33-18C strain (an aureobasidin-resistant type).

Thus, the cells were suspended in 0.1M lithium acetate solution (pH: 7.5), 5 μg of pYCAR2LZ and 850 μl of 40% polyethylene glycol (containing 0.1M of lithium acetate) were added thereto, the mixture was allowed to stand at 30° C. for 30 minutes, processed at 42° C. for 15 minutes and centrifuged and the collected cells were incubated in 5 ml of a YPD liquid medium (containing 1% of yeast extract, 2% of polypeptone and 2% of glucose) for one hour. The cultured liquid was inoculated on SD agar medium (a uracil-free minimum agar medium; containing 0.67% of amino acid-free yeast nitrogen base, 2% of glucose and 2% of agar) and incubated at 30° C. After three to four days, transformants which became to require no uracil were obtained. Then those transformants were inoculated on a plate [which was an SD agar medium or a YPD agar medium containing 0.004% of X-gal and 0.1M of potassium phosphate buffer (pH: 7.0)] for testing the lacZ expression. After incubating at 30° C. for two to three days, the color developments in blue of transformant's colony were compared whereby it was noted that the transformant obtained from S. cerevisiae SH3328 strain was in light blue while that obtained from S. cerevisiae AL33-18C strain formed blue to dark blue colonies. Thus, it was confirmed that expression of β-galactosidase by the promoter of scaur2 gene significantly increased in the resistant strain. An increase in the expression in the resistant strain was further confirmed by measuring the β-galactosidase activity. For measuring the activity, each of the transformants was incubated overnight in a YPD slant at 30° C. Cells were scratched off and suspended in a saline solution to make $OD_{600}$ about 15. The cell suspension (100 μl) was mixed with glass beads (425–600 microns; manufactured by Sigma) and the cells were homogenized using a vortex stirrer (30 seconds; for three times) with ice cooling. Then a Z buffer (containing 0.1M of sodium phosphate buffer (pH: 7.0), 0.01M of KCl, 1 mM of $MgSO_4$ and 0.05M of 2-mercaptoethanol] was added to the homogenate to make the total volume 1 ml. The homogenate (0.5 ml) was used for measuring the galactosidase activity using an ONPG as a substrate [Experiments in Molecular Biology, pages 352–355, Cold Spring Harbor Laboratory, 1972]. Thus, 0.5 ml of a cell homogenate and 0.5 ml of a Z buffer were mixed, the mixture was kept at 28° C. for five minutes and 0.2 ml of an ONPG solution [4 mg/ml 0.1M phosphate buffer (pH: 7.0)] was added to initiate the enzymatic reaction. This was kept at 28° C. for 20–40 minutes and then the reaction was stopped by adding 0.5 ml of 1M $Na_2CO_3$ thereto. After this was centrifuged at 10,000 rpm for one minute, $OD_{420}$ and $OD_{550}$ of the supernatant liquid were measured. Activity was calculated by the following expression.

$$\text{Activity (unit/}OD_{600}) = 1000 \times OD_{420-1.75} \times OD_{550}/t \times v \times OD_{600}$$

in which $OD_{420}$, $OD_{550}$: measured in the supernatant liquid of the reaction solution $OD_{600}$: cell concentration of the cell suspension t: reaction time (minute)

v: amount (ml) of the cell suspension used for the reaction

The results are given in Table 4. As shown in Table 4, expression of β-galactosidase by the promoter of scaur2 gene was as high as about 20-fold in the aureobasidin-resistant S. cerevisiae AL33–18C strain as compared with that in the wild-type strain (S. cerevisiae SH3328 strain).

TABLE 4

| | Activity (units/$OD_{600}$) |
|---|---|
| Wild-type strain (S. cerevisiae SH3328) having pYCAR2LZ | |
| Clone 1 | 2.12 |
| Clone 2 | 1.99 |
| Clone 3 | 2.09 |
| Clone 4 | 1.86 |
| Clone 5 | 2.28 |
| Resistant Strain (S. cerevisiae AL33-18C) having pYCAR2LZ | |
| Clone 1 | 36.6 |
| Clone 2 | 54.4 |
| Clone 3 | 48.6 |
| Clone 4 | 53.8 |
| Clone 5 | 45.7 |

EXAMPLE 5

Identification of resistant gene of an aureobasidin-resistant S. cerevisiae AL33-18C strain.

When genetic analysis of S. cerevisiae AL33-18C strain was conducted, resistant gene was found to be present near the centromere of the seventh chromosome and, as a result of the further tetrad analysis, it was found to be present near an LEU1 gene marker [<4.1 cM (centimorgans)]. Since a PDR1 gene which has been known as a pleiotropic drug resistance gene is present at this position, it is now clear that a mutation took place in a PDR1 gene in the case of this *S. cerevisiae* AL33-18C strain. PDR1 gene and scaur2 gene are entirely different genes and, in addition, the product of the PDR1 gene has been known as a factor for a transcriptional control whereby it was found that the PDR1 gene product controlled the transcription of the scaur2 gene.

As mentioned hereinabove, the present invention offers a promoter being capable of controlling the transcription which is useful for the manufacture of heterologous proteins and metabolites using a gene recombination technique. Said promoter can be used in a complete nutrient medium and, further, its transcriptional control is possible by a PDR1 gene product.

The above-mentioned *Aureobasidium pullulans* No. R106 strain has been designated by such a name and deposited at the National Institute of Bioscience and Human Technology, Agency of Industrial Science and Technology, MITI (located at 1-3, Higashi-1-chome, Tsukuba City, Ibaragi Prefecture 305, Japan) under the accession number FERM BP-1938 on Jul. 8, 1988 in accordance with the Budapest Treaty.

Further, the above-mentioned *E. coli* HB101 possessing a plasmid pSCAR2 has been named and designated as *Escherichia coli* HB101/pSCAR2 and deposited at the National Institute of Bioscience and Human Technology, Agency of Industrial Science and Technology, MITI (located at 1-3, Higashi-1-chome, Tsukuba City, Ibaragi Prefecture 305, Japan) under the accession number FERM BP-4484 (original date of deposition: April 13, 1993; date of request for the transfer to an international deposition: Dec. 1, 1993).

What is claimed is:

1. An isolated DNA which comprises a nucleic acid sequence of SEQ ID NO:1.
2. A DNA according to claim 1 wherein said DNA is transcriptionally controllable by a PDR1 gene product.
3. An isolated DNA which is hybridizable to the DNA of claim 1 at 65° C. for 20 hours in a solution containing 6×SSC, 1% sodium laurylsulfate, 100 μg/ml of salmon sperm DNA and 5×Denhardt's solution and has a promoter activity in yeast.
4. A DNA according to claim 1 wherein a heterologous gene is linked in an expressible manner.
5. A DNA according to claim 4 wherein the heterologous gene is a nucleic acid encoding protein, antisense RNA, a decoy, or a ribozyme.
6. A vector containing a DNA according to claim 1.
7. A vector according to claim 6 wherein the vector is a plasmid vector or a virus vector.
8. A yeast into which a DNA of claim 4 is introduced.
9. A yeast which is transformed by a vector of claim 6.
10. A method for the manufacture of a protein by yeast, which comprises incubating yeast which is transformed by a vector comprising the DNA according to claim 5, and harvesting the protein.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1366
      (B) TYPE: nucleic acid
      (C) STRANDEDNESS: double
      (D) TOPOLOGY: linear    (ii) MOLECULE TYPE: genomic DNA    (xi) SEQUENCE DESCRIPTION: SEQ ID NO:1:

```
TCCAACCCTG CGCATTCACC ATTATCAAAC TCGTCTTTTT TGTCTTTACG TTTTAATTTA      60

GCACCGAGCC CAACGTTGTC GTCCTTAATT GACACTTTGA TATGCGAAGT GTTCGAATTC     120

ATGGGGGATA ACCCCAGACC CATACCGGGT TTCCATCCAA ACTTTTCTAG AAATTGGTGC     180

CCGAATCTCG AGGTGTCGTT ACTCCATGCC GTATTTCTGG GGTCTAAACC AAACCGCTGT     240

TTGGTTCTTG TAGCTGCCAA ACCCATTCTG CTTCTTTGTT TAATGGTGTA AGCTGCCTAT     300

ATGTTACTAT TGAGTACTCA TCTCATCGCT TCTTTCAGAA CAAAATTTTT CATATTTTTT     360

TTTTTTCCTT TTCTTTTTTT TTTTTTCTTT GACTGTTACC CGGTTGTTTA TATTTGTAGG     420

AAAACAACAA CGACAGAGAA AATATCCTTG CAGTGGCGGC TAATTTGTTA GTTGACTGAT     480

TGATCACCTT CACTTATTAA AGTAAAATCA GCATACAAGA GATCAGAAGG GAGAAAGAGA     540

GTGGGCAAGG CTATAGTACT TTGAAGAAAG CATCTTTGAA CCGACTAGTT CTCTTCACAA     600

GCAAAATCTA TATGACTAAC CGCAAGGGGC AAAGGGTTGT GAGAGGGCCC GTCTTTCTCC     660

CGCTATAGCC GTCACTGGTA TCCCTCCTGG CTGCACAAAT CCGATAGAAA GGGGAAGAAG     720

GAAGTTTAGT GCCACCTTAT AGCACGCAGT TACTGTTTAC GCTAAGGAGA GGCATACTCA     780

ATTTTTATTA GTCGCCTTCT TTAGTTGCTG CGTTTTTATC CACGGTTCTC TACTAAATGC     840

TTGCGATAAG CGCTTCTATT TTCCTCCCCA CCGCGAGGCG GAAATGGCAC ATTTTTTTTC     900

TTTTGCTTCT GTGCTTTTGC TGTAATTTTT GGCATGTGCT ATTGTATGAA GATAACGCGT     960

GGTTCCGTGG AAATAGCCGG AAATTTTGCC GGGAATATGA CGGACATGAT TTAACACCCG    1020

TGGAAATGAA AAAAGCCAAG GTAAGAAAGT GGCAATATTT TTCCTACAAA TAGATCTGCT    1080

GTCCCTTAGA TGATTACCAT ACATATATAT ATTTATTACA CACATCTGTC AGAGGTAGCT    1140
```

```
AGCGAAGGTG TCACTGAAAT ATTTTTTGTT CCAGTTAGTA TAAATACGGA GGTAGAACAG    1200

CTCTCCGCGT GTATATCTTT TTTTGCGCTA TACAAGAACA GGAAGAACGC ATTTCCATAC    1260

CTTTTTCTCC TTACAGGTGC CCTCTGAGTA GTGTCACGAA CGAGGAAAAA GATTAATATT    1320

ACTGTTTTTA TATTCAAAAA GAGTAAAGCC GTTGCTATAT ACGAAT                   1366

(2) INFORMATION FOR SEQ ID NO:2:

(i) SEQUENCE CHARACTERISTICS:
        (A) LENGTH: 5340
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:2:

AGCGCTTCTA TTTTCCTCCC CACCGCGAGG CGGAAATGGC ACATTTTTTT TCTTTTGCTT      60

CTGTGCTTTT GCTGTAATTT TTGGCATGTG CTATTGTATG AAGATAACGC GTGGTTCCGT     120

GGAAATAGCC GGAAATTTTG CCGGGAATAT GACGGACATG ATTTAACACC CGTGGAAATG     180

AAAAAAGCCA AGGTAAGAAA GTGGCAATAT TTTTCCTACA AATAGATCTG CTGTCCCTTA     240

GATGATTACC ATACATATAT ATATTTATTA CACACATCTG TCAGAGGTAG CTAGCGAAGG     300

TGTCACTGAA ATATTTTTTG TTCCAGTTAG TATAAATACG GAGGTAGAAC AGCTCTCCGC     360

GTGTATATCT TTTTTTGCGC TATACAAGAA CAGGAAGAAC GCATTTCCAT ACCTTTTTCT     420

CCTTACAGGT GCCCTCTGAG TAGTGTCACG AACGAGGAAA AAGATTAATA TTACTGTTTT     480

TATATTCAAA AAGAGTAAAG CCGTTGCTAT ATACGAATAT GACGATTACC GTGGGGATG      540

CAGTTTCGGA GACGGAGCTG GAAAACAAAA GTCAAAACGT GGTACTATCT CCCAAGGCAT     600

CTGCTTCTTC AGACATAAGC ACAGATGTTG ATAAAGCACA ATCGTCTTCT TGGGATGACA     660

AATCTTTGCT GCCTACAGGT GAATATATTG TGGACAGAAA TAAGCCCCAA ACCTACTTGA     720

ATAGCGATGA TATCGAAAAA GTGACAGAAT CTGATATTTT CCCTCAGAAA CGTCTGTTTT     780

CATTCTTGCA CTCTAAGAAA ATTCCAGAAG TACCACAAAC CGATGACGAG AGGAAGATAT     840

ATCCTCTGTT CCATACAAAT ATTATCTCTA ACATGTTTTT TTGGTGGGTT CTACCCATCC     900

TGCGAGTTGG TTATAAGAGA ACGATACAGC CGAACGATCT CTTCAAAATG GATCCGAGGA     960

TGTCTATAGA GACCCTTTAT GACGACTTTG AAAAAAACAT GATTTACTAT TTGAGAAGA    1020

CGAGGAAAAA ATACCGTAAA AGACATCCAG AAGCGACAGA AGAAGAGGTT ATGGAAAATG    1080

CCAAACTACC TAAACATACA GTTCTGAGAG CTTTATTATT CACTTTTAAG AAACAGTACT    1140

TCATGTCGAT AGTGTTTGCA ATTCTCGCTA ATTGTACATC CGGTTTTAAC CCCATGATTA    1200

CCAAGAGGCT AATTGAGTTT GTCGAAGAAA AGGCTATTTT TCATAGCATG CATGTTAACA    1260

AAGGTATTGG TTACGCTATT GGTGCATGTT TGATGATGTT CGTTAACGGG TTGACGTTCA    1320

ATCATTTCTT TCATACATCC CAACTGACTG GTGTGCAAGC TAAGTCTATT CTTACTAAAG    1380

CTGCCATGAA GAAAATGTTT AATGCATCTA ATTATGCGAG ACATTGTTTT CCTAACGGTA    1440

AAGTGACTTC TTTTGTAACA ACAGATCTCG CTAGAATTGA ATTTGCCTTA TCTTTTCAGC    1500

CGTTTTTGGC TGGGTTCCCT GCAATTTTGG CTATTTGCAT TGTTTTATTG ATCGTTAACC    1560

TTGGACCCAT TGCCTTAGTT GGGATTGGTA TTTTTTTCGG TGGGTTTTTC ATATCCTTAT    1620

TTGCATTTAA GTTAATTCTG GGCTTTAGAA TTGCTGCGAA CATCTTCACT GATGCTAGAG    1680

TTACCATGAT GAGAGAAGTG CTGAATAATA TAAAAATGAT TAAATATTAT ACGTGGGAGG    1740
```

-continued

```
ATGCGTATGA AAAAAATATT CAAGATATTA GGACCAAAGA GATTTCTAAA GTTAGAAAAA     1800

TGCAACTATC AAGAAATTTC TTGATTGCTA TGGCCATGTC TTTGCCTAGT ATTGCTTCAT     1860

TGGTCACTTT CCTTGCAATG TACAAAGTTA ATAAAGGAGG CAGGCAACCT GGTAATATTT     1920

TTGCCTCTTT ATCTTTATTT CAGGTCTTGA GTTTGCAAAT GTTTTTCTTA CCTATTGCTA     1980

TTGGTACTGG AATTGACATG ATCATTGGAT TGGGCCGTTT GCAAAGCTTA TTGGAGGCTC     2040

CAGAAGATGA TCCAAATCAG ATGATTGAAA TGAAGCCCTC TCCTGGCTTT GATCCAAAAT     2100

TGGCTCTAAA AATGACACAT TGCTCATTTG AGTGGGAAGA TTATGAATTA AACGACGCTA     2160

TTGAAGAAGC AAAAGGAGAA GCTAAAGATG AAGGTAAAAA GAACAAAAAA AAGCGTAAGG     2220

ATACATGGGG TAAGCCATCT GCAAGTACTA ATAAGGCGAA AAGATTGGAC AATATGTTGA     2280

AAGACAGAGA CGGCCCGGAA GATTTAGAAA AAACTTCGTT TAGGGGTTTC AAGGACTTGA     2340

ACTTCGATAT TAAAAAGGGC GAATTTATTA TGATTACGGG ACCTATTGGT ACTGGTAAAT     2400

CTTCATTATT GAATGCGATG GCAGGATCAA TGAGAAAAAT TGATGGTAAG GTTGAAGTCA     2460

ACGGGGACTT ATTAATGTGT GGTTATCCAT GGATTCAAAA TGCATCTGTA AGAGATAACA     2520

TCATATTCGG TTCACCATTC AATAAAGAAA AGTATGATGA AGTAGTTCGT GTTTGCTCTT     2580

TGAAAGCTGA TCTGGATATT TTACCGGCAG GCGATATGAC CGAAATTGGG GAACGTGGTA     2640

TTACTTTATC TGGTGGTCAA AAGGCACGTA TCAATTTAGC CAGGTCTGTT TATAAGAAGA     2700

AGGATATTTA TGTATTCGAC GATGTCCTAA GTGCTGTCGA TTCTCGTGTT GGTAAACACA     2760

TCATGGATGA ATGTCTAACC GGAATGCTTG CTAATAAAAC CAGAATTTTA GCAACGCATC     2820

AGTTGTCACT GATTGAGAGA GCTTCTAGAG TCATCGTTTT AGGTACTGAT GGCCAAGTCG     2880

ATATTGGTAC TGTTGATGAG CTAAAAGCTC GTAATCAAAC TTTGATAAAT CTTTTACAAT     2940

TCTCTTCTCA AAATTCGGAG AAAGAGGATG AAGAACAGGA AGCGGTTGTT CCGGTGAAT      3000

TGGGACAACT AAAAATATGAA CCAGAGGTAA AGGAATTGAC TGAACTGAAG AAAAAGGCTA     3060

CAGAAATGTC ACAAACTGCA ATAGTGGTA AAATTGTAGC GGATGGTCAT ACTAGTAGTA      3120

AAGAAGAAAG AGCAGTCAAT AGTATCAGTC TGAAAATATA CCGTGAATAC ATTAAAGCTG     3180

CAGTAGGTAA GTGGGGTTTT ATCGCACTAC CGTTGTATGC AATTTTAGTC GTTGGAACCA     3240

CATTCTGCTC ACTTTTTTCT TCCGTTTGGT TATCTTACTG GACTGAGAAT AAATTCAAAA     3300

ACAGACCACC CAGTTTTTAT ATGGGTCTTT ACTCCTTCTT TGTGTTTGCT GCTTTCATAT     3360

TCATGAATGG CCAGTTCACC ATACTTTGCG CAATGGGTAT TATGGCATCG AAATGGTTAA     3420

ATTTGAGGGC TGTGAAAAGA ATTTTACACA CTCCAATGTC ATACATAGAT ACCACACCTT     3480

TGGGACGTAT TCTGAACAGA TTCACAAAAG ATACAGATAG CTTAGATAAT GAGTTAACCG     3540

AAAGTTTACG GTTGATGACA TCTCAATTTG CTAATATTGT AGGTGTTTGC GTCATGTGTA     3600

TTGTTTACTT GCCGTGGTTT GCTATCGCAA TTCCGTTTCT TTTGGTCATC TTTGTTCTGA     3660

TTGCTGATCA TTATCAGAGT TCTGGTAGAG AAATTAAAAG ACTTGAAGCT GTGCAACGGT     3720

CTTTTGTTTA CAATAATTTA AATGAAGTTT GGGTGGGAT GGATACAATC AAAGCATACC     3780

GAAGTCAGGA ACGATTTTTG GCGAAATCAG ATTTTTTGAT CAACAAGATG AATGAGGCGG     3840

GATACCTTGT AGTTGTCCTG CAAAGATGGG TAGGTATTTT CCTTGATATG GTTGCTATCG     3900

CATTTGCACT AATTATTACG TTATTGTGTG TTACGAGAGC CTTTCCTATT TCCGCGGCTT     3960

CAGTTGGTGT TTTGTTGACT TATGTATTAC AATTGCCTGG TCTATTAAAT ACCATTTTAA     4020

GGGCAATGAC TCAAACAGAG AATGACATGA ATAGTGCCGA AGATTGGTA ACATATGCAA      4080

CTGAACTACC ACTAGAGGCA TCCTATAGAA AGCCCGAAAT GACACCTCCA GAGTCATGGC     4140
```

```
CCTCAATGGG CGAAATAATT TTTGAAAATG TTGATTTTGC CTATAGACCT GGTTTACCTA    4200

TAGTTTTAAA AAATCTTAAC TTGAATATCA AGAGTGGGGA AAAAATTGGT ATCTGTGGTC    4260

GTACAGGTGC TGGTAAGTCC ACTATTATGA GTGCCCTTTA CAGGTTGAAT GAATTGACCG    4320

CAGGTAAAAT TTTAATTGAC AATGTTGATA TAAGTCAGCT GGGACTTTTC GATTTAAGAA    4380

GAAAATTAGC CATCATTCCA CAAGATCCAG TATTATTTAG GGGTACGATT CGCAAGAACT    4440

TAGATCCATT TAATGAGCGT ACAGATGACG AATTATGGGA TGCATTGGTG AGAGGTGGTG    4500

CTATCGCCAA GGATGACTTG CCGGAAGTGA AATTGCAAAA ACCTGATGAA AATGGTACTC    4560

ATGGTAAAAT GCATAAGTTC CATTTAGATC AAGCAGTGGA AGAAGAGGGC TCCAATTTCT    4620

CCTTAGGTGA GAGACAACTA TTAGCATTAA CAAGGGCATT GGTCCGCCAA TCAAAAATAT    4680

TGATTTTGGA TGAGGCTACA TCCTCAGTGG ACTACGAAAC GGATGGCAAA ATCCAAACAC    4740

GTATTGTTGA GGAATTTGGA GATTGTACAA TTTTGTGTAT TGCTCACAGA CTGAAGACCA    4800

TTGTAAATTA TGATCGTATT CTTGTTTTAG AGAAGGGTGA AGTCGCAGAA TTCGATACAC    4860

CATGGACGTT GTTTAGTCAA GAAGATAGTA TTTTCAGAAG CATGTGTTCT AGATCTGGTA    4920

TTGTGGAAAA TGATTTCGAG AACAGAAGTT AATTTATATT ATTTGTTGCA TGATTTTTCT    4980

CTTTTATTTA TTTATATGTT GCCGATGGTA CAAATTAGTA CTAGAAAAGA AAACCCACTA    5040

CTATGACTTG CAGAAAAAGT TATGTGTGCC ATAGATAGAT ATAATTGCAT ACCCACATCG    5100

TATACTCAAA ATTCCGAAAA GAACATTTCA TTTTTTATGA GGCAAACTGA ACAACGCTTC    5160

GGTCCTTTTT TCATTCTAGA AATATATATT TATACATCAT TTTCAGAAGA TATTCAAAGA    5220

ACTTATTGGG ATGTCTATTT ACTGAATAAA GTATACACAA AAAACGAATT TAAAATGGAA    5280

GGCATAAATA GAAAACTTAG AAGTGAAAAT CCTAAAACCG AAGGATATTT CAAATACGTA    5340
```

(2) INFORMATION FOR SEQ ID NO:3:

(i) SEQUENCE CHARACTERISTICS:
        (A) LENGTH: 1477
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:3:

```
Met Thr Ile Thr Val Gly Asp Ala Val Ser Glu Thr Leu Glu
              5                  10                  15

Asn Lys Ser Gln Asn Val Val Leu Ser Pro Lys Ala Ser Ala Ser
             20                  25                  30

Ser Asp Ile Ser Thr Asp Val Asp Lys Asp Thr Ser Ser Ser Trp
             35                  40                  45

Asp Asp Lys Ser Leu Leu Pro Thr Gly Glu Tyr Ile Val Asp Arg
             50                  55                  60

Asn Lys Pro Gln Thr Tyr Leu Asn Ser Asp Ile Glu Lys Val
             65                  70                  75

Thr Glu Ser Asp Ile Phe Pro Gln Lys Arg Leu Phe Ser Phe Leu
             80                  85                  90

His Ser Lys Lys Ile Pro Glu Val Pro Gln Thr Asp Asp Glu Arg
             95                 100                 105

Lys Ile Tyr Pro Leu Phe His Thr Asn Ile Ile Ser Asn Met Phe
            110                 115                 120

Phe Trp Trp Val Leu Pro Ile Leu Arg Val Gly Tyr Lys Arg Thr
```

-continued

```
                125                 130                 135
Ile Gln Pro Asn Asp Leu Phe Lys Met Asp Pro Arg Met Ser Ile
                140                 145                 150

Glu Thr Leu Tyr Asp Asp Phe Glu Lys Asn Met Ile Tyr Tyr Phe
                155                 160                 165

Glu Lys Thr Arg Lys Lys Tyr Arg Lys Arg His Pro Glu Ala Thr
                170                 175                 180

Glu Glu Glu Val Met Glu Asn Ala Lys Leu Pro Lys His Thr Val
                185                 190                 195

Leu Arg Ala Leu Leu Phe Thr Phe Lys Lys Gln Tyr Phe Met Ser
                200                 205                 210

Ile Val Phe Ala Ile Leu Ala Asn Cys Thr Ser Gly Phe Asn Pro
                215                 220                 225

Met Ile Thr Lys Arg Leu Ile Glu Phe Val Glu Glu Lys Ala Ile
                230                 235                 240

Phe His Ser Met His Val Asn Lys Gly Ile Gly Tyr Ala Ile Gly
                245                 250                 255

Ala Cys Leu Met Met Phe Val Asn Gly Leu Thr Phe Asn His Phe
                260                 265                 270

Phe His Thr Ser Gln Leu Thr Gly Val Gln Ala Lys Ser Ile Leu
                275                 280                 285

Thr Lys Ala Ala Met Lys Lys Met Phe Asn Ala Ser Asn Tyr Ala
                290                 295                 300

Arg His Cys Phe Pro Asn Gly Lys Val Thr Ser Phe Val Thr Thr
                305                 310                 315

Asp Leu Ala Arg Ile Glu Phe Ala Leu Ser Phe Gln Pro Phe Leu
                320                 325                 330

Ala Gly Phe Pro Ala Ile Leu Ala Ile Cys Ile Val Leu Leu Ile
                335                 340                 345

Val Asn Leu Gly Pro Ile Ala Leu Val Gly Ile Gly Ile Phe Phe
                350                 355                 360

Gly Gly Phe Phe Ile Ser Leu Phe Ala Phe Lys Leu Ile Leu Gly
                365                 370                 375

Phe Arg Ile Ala Ala Asn Ile Phe Thr Asp Ala Arg Val Thr Met
                380                 385                 390

Met Arg Glu Val Leu Asn Asn Ile Lys Met Ile Lys Tyr Tyr Thr
                395                 400                 405

Trp Glu Asp Ala Tyr Glu Lys Asn Ile Gln Asp Ile Arg Thr Lys
                410                 415                 420

Glu Ile Ser Lys Val Arg Lys Met Gln Leu Ser Arg Asn Phe Leu
                425                 430                 435

Ile Ala Met Ala Met Ser Leu Pro Ser Ile Ala Ser Leu Val Thr
                440                 445                 450

Phe Leu Ala Met Tyr Lys Val Asn Lys Gly Gly Arg Gln Pro Gly
                455                 460                 465

Asn Ile Phe Ala Ser Leu Ser Leu Phe Gln Val Leu Ser Leu Gln
                470                 475                 480

Met Phe Phe Leu Pro Ile Ala Ile Gly Thr Gly Ile Asp Met Ile
                485                 490                 495

Ile Gly Leu Gly Arg Leu Gln Ser Leu Leu Glu Ala Pro Glu Asp
                500                 505                 510

Asp Pro Asn Gln Met Ile Glu Met Lys Pro Ser Pro Gly Phe Asp
                515                 520                 525
```

-continued

```
Pro Lys Leu Ala Leu Lys Met Thr His Cys Ser Phe Glu Trp Glu
                530                 535                 540
Asp Tyr Glu Leu Asn Asp Ala Ile Glu Glu Ala Lys Gly Glu Ala
                545                 550                 555
Lys Asp Glu Gly Lys Lys Asn Lys Lys Lys Arg Lys Asp Thr Trp
                560                 565                 570
Gly Lys Pro Ser Ala Ser Thr Asn Lys Ala Lys Arg Leu Asp Asn
                575                 580                 585
Met Leu Lys Asp Arg Asp Gly Pro Glu Asp Leu Glu Lys Thr Ser
                590                 595                 600
Phe Arg Gly Phe Lys Asp Leu Asn Phe Asp Ile Lys Lys Gly Glu
                605                 610                 615
Phe Ile Met Ile Thr Gly Pro Ile Gly Thr Gly Lys Ser Ser Leu
                620                 625                 630
Leu Asn Ala Met Ala Gly Ser Met Arg Lys Ile Asp Gly Lys Val
                635                 640                 645
Glu Val Asn Gly Asp Leu Leu Met Cys Gly Tyr Pro Trp Ile Gln
                650                 655                 660
Asn Ala Ser Val Arg Asp Asn Ile Ile Phe Gly Ser Pro Phe Asn
                665                 670                 675
Lys Glu Lys Tyr Asp Glu Val Val Arg Val Cys Ser Leu Lys Ala
                680                 685                 690
Asp Leu Asp Ile Leu Pro Ala Gly Asp Met Thr Glu Ile Gly Glu
                695                 700                 705
Arg Gly Ile Thr Leu Ser Gly Gly Gln Lys Ala Arg Ile Asn Leu
                710                 715                 720
Ala Arg Ser Val Tyr Lys Lys Lys Asp Ile Tyr Val Phe Asp Asp
                725                 730                 735
Val Leu Ser Ala Val Asp Ser Arg Val Gly Lys His Ile Met Asp
                740                 745                 750
Glu Cys Leu Thr Gly Met Leu Ala Asn Lys Thr Arg Ile Leu Ala
                755                 760                 765
Thr His Gln Leu Ser Leu Ile Glu Arg Ala Ser Arg Val Ile Val
                770                 775                 780
Leu Gly Thr Asp Gly Gln Val Asp Ile Gly Thr Val Asp Glu Leu
                785                 790                 795
Lys Ala Arg Asn Gln Thr Leu Ile Asn Leu Leu Gln Phe Ser Ser
                800                 805                 810
Gln Asn Ser Glu Lys Glu Asp Glu Gln Glu Ala Val Val Ser
                815                 820                 825
Gly Glu Leu Gly Gln Leu Lys Tyr Glu Pro Glu Val Lys Glu Leu
                830                 835                 840
Thr Glu Leu Lys Lys Lys Ala Thr Glu Met Ser Gln Thr Ala Asn
                845                 850                 855
Ser Gly Lys Ile Val Ala Asp Gly His Thr Ser Ser Lys Glu Glu
                860                 865                 870
Arg Ala Val Asn Ser Ile Ser Leu Lys Ile Tyr Arg Glu Tyr Ile
                875                 880                 885
Lys Ala Ala Val Gly Lys Trp Gly Phe Ile Ala Leu Pro Leu Tyr
                890                 895                 900
Ala Ile Leu Val Val Gly Thr Thr Phe Cys Ser Leu Phe Ser Ser
                905                 910                 915
```

-continued

Val Trp Leu Ser Tyr Trp Thr Glu Asn Lys Phe Lys Asn Arg Pro
            920                 925                 930

Pro Ser Phe Tyr Met Gly Leu Tyr Ser Phe Val Phe Ala Ala
            935                 940                 945

Phe Ile Phe Met Asn Gly Gln Phe Thr Ile Leu Cys Ala Met Gly
            950                 955                 960

Ile Met Ala Ser Lys Trp Leu Asn Leu Arg Ala Val Lys Arg Ile
            965                 970                 975

Leu His Thr Pro Met Ser Tyr Ile Asp Thr Thr Pro Leu Gly Arg
            980                 985                 990

Ile Leu Asn Arg Phe Thr Lys Asp Thr Asp Ser Leu Asp Asn Glu
            995                 1000                1005

Leu Thr Glu Ser Leu Arg Leu Met Thr Ser Gln Phe Ala Asn Ile
            1010                1015                1020

Val Gly Val Cys Val Met Cys Ile Val Tyr Leu Pro Trp Phe Ala
            1025                1030                1035

Ile Ala Ile Pro Phe Leu Leu Val Ile Phe Val Leu Ile Ala Asp
            1040                1045                1050

His Tyr Gln Ser Ser Gly Arg Glu Ile Lys Arg Leu Glu Ala Val
            1055                1060                1065

Gln Arg Ser Phe Val Tyr Asn Asn Leu Asn Glu Val Leu Gly Gly
            1070                1075                1080

Met Asp Thr Ile Lys Ala Tyr Arg Ser Gln Glu Arg Phe Leu Ala
            1085                1090                1095

Lys Ser Asp Phe Leu Ile Asn Lys Met Asn Glu Ala Gly Tyr Leu
            1100                1105                1110

Val Val Val Leu Gln Arg Trp Val Gly Ile Phe Leu Asp Met Val
            1115                1120                1125

Ala Ile Ala Phe Ala Leu Ile Ile Thr Leu Leu Cys Val Thr Arg
            1130                1135                1140

Ala Phe Pro Ile Ser Ala Ala Ser Val Gly Val Leu Leu Thr Tyr
            1145                1150                1155

Val Leu Gln Leu Pro Gly Leu Leu Asn Thr Ile Leu Arg Ala Met
            1160                1165                1170

Thr Gln Thr Glu Asn Asp Met Asn Ser Ala Glu Arg Leu Val Thr
            1175                1180                1185

Tyr Ala Thr Glu Leu Pro Leu Glu Ala Ser Tyr Arg Lys Pro Glu
            1190                1195                1200

Met Thr Pro Pro Glu Ser Trp Pro Ser Met Gly Glu Ile Ile Phe
            1205                1210                1215

Glu Asn Val Asp Phe Ala Tyr Arg Pro Gly Leu Pro Ile Val Leu
            1220                1225                1230

Lys Asn Leu Asn Leu Asn Ile Lys Ser Gly Glu Lys Ile Gly Ile
            1235                1240                1245

Cys Gly Arg Thr Gly Ala Gly Lys Ser Thr Ile Met Ser Ala Leu
            1250                1255                1260

Tyr Arg Leu Asn Glu Leu Thr Ala Gly Lys Ile Leu Ile Asp Asn
            1265                1270                1275

Val Asp Ile Ser Gln Leu Gly Leu Phe Asp Leu Arg Arg Lys Leu
            1280                1285                1290

Ala Ile Ile Pro Gln Asp Pro Val Leu Phe Arg Gly Thr Ile Arg
            1295                1300                1305

Lys Asn Leu Asp Pro Phe Asn Glu Arg Thr Asp Asp Glu Leu Trp

```
                    1310                 1315                 1320
Asp Ala Leu Val Arg Gly Gly Ala Ile Ala Lys Asp Asp Leu Pro
            1325                 1330                 1335
Glu Val Lys Leu Gln Lys Pro Asp Glu Asn Gly Thr His Gly Lys
            1340                 1345                 1350
Met His Lys Phe His Leu Asp Gln Ala Val Glu Glu Glu Gly Ser
            1355                 1360                 1365
Asn Phe Ser Leu Gly Glu Arg Gln Leu Leu Ala Leu Thr Arg Ala
            1370                 1375                 1380
Leu Val Arg Gln Ser Lys Ile Leu Ile Leu Asp Glu Ala Thr Ser
            1385                 1390                 1395
Ser Val Asp Tyr Glu Thr Asp Gly Lys Ile Gln Thr Arg Ile Val
            1400                 1405                 1410
Glu Glu Phe Gly Asp Cys Thr Ile Leu Cys Ile Ala His Arg Leu
            1415                 1420                 1425
Lys Thr Ile Val Asn Tyr Asp Arg Ile Leu Val Leu Glu Lys Gly
            1430                 1435                 1440
Glu Val Ala Glu Phe Asp Thr Pro Trp Thr Leu Phe Ser Gln Glu
            1445                 1450                 1455
Asp Ser Ile Phe Arg Ser Met Cys Ser Arg Ser Gly Ile Val Glu
            1460                 1465                 1470
Asn Asp Phe Glu Asn Arg Ser
            1475

(2) INFORMATION FOR SEQ ID NO:4:

(i) SEQUENCE CHARACTERISTICS:
         (A) LENGTH: 1512
         (B) TYPE: nucleic acid
         (C) STRANDEDNESS: double
         (D) TOPOLOGY: linear (ii) MOLECULE TYPE: genomic DNA (xi) SEQUENCE DESCRIPTION: SEQ ID NO:4:

GGATCCCACG TGCTTGCTAA ACTTCACCCT TCACAAAATG GATACCCCAT TTTCCGTCAA       60

TAATCTTCTG CTTTCTCTGC GTGTCCAATT CCTCTGATAT TTTGCTTTCC TTTCCGTTCA      120

GCCTACCAAG AATTCGCTGG AAGACATCCA ACCCTGCGCA TTCACCATTA TCAAACTCGT      180

CTTTTTTGTC TTTACGTTTT AATTTAGCAC CGAGCCCAAC GTTGTCGTCC TTAATTGACA      240

CTTTGATATG CGAAGTGTTC GAATTCATGG GGATAACCC CAGACCCATA CCGGGTTTCC      300

ATCCAAACTT TTCTAGAAAT TGGTGCCCGA ATCTCGAGGT GTCGTTACTC CATGCCGTAT      360

TTCTGGGGTC TAAACCAAAC CGCTGTTTGG TTCTTGTAGC TGCCAAACCC ATTCTGCTTC      420

TTTGTTTAAT GGTGTAAGCT GCCTATATGT TACTATTGAG TACTCATCTC ATCGCTTCTT      480

TCAGAACAAA ATTTTTCATA TTTTTTTTTT TTCCTTTTCT TTTTTTTTTT TTCTTTGACT      540

GTTACCCGGT TGTTTATATT TGTAGGAAAA CAACAACGAC AGAGAAAATA TCCTTGCAGT      600

GGCGGCTAAT TTGTTAGTTG ACTGATTGAT CACCTTCACT TATTAAAGTA AAATCAGCAT      660

ACAAGAGATC AGAAGGGAGA AAGAGAGTGG GCAAGGCTAT AGTACTTTGA AGAAAGCATC      720

TTTGAACCGA CTAGTTCTCT TCACAAGCAA AATCTATATG ACTAACCGCA AGGGGCAAAG      780

GGTTGTGAGA GGGCCCGTCT TTCTCCCGCT ATAGCCGTCA CTGGTATCCC TCCTGGCTGC      840

ACAAATCCGA TAGAAAGGGG AAGAAGGAAG TTTAGTGCCA CCTTATAGCA CGCAGTTACT      900

GTTTACGCTA AGGAGAGGCA TACTCAATTT TTATTAGTCG CCTTCTTTAG TTGCTGCGTT      960
```

```
TTTATCCACG GTTCTCTACT AAATGCTTGC GATAAGCGCT TCTATTTTCC TCCCCACCGC    1020

GAGGCGGAAA TGGCACATTT TTTTTCTTTT GCTTCTGTGC TTTTGCTGTA ATTTTTGGCA    1080

TGTGCTATTG TATGAAGATA ACGCGTGGTT CCGTGGAAAT AGCCGGAAAT TTTGCCGGGA    1140

ATATGACGGA CATGATTTAA CACCCGTGGA AATGAAAAAA GCCAAGGTAA GAAAGTGGCA    1200

ATATTTTTCC TACAAATAGA TCTGCTGTCC CTTAGATGAT TACCATACAT ATATATATTT    1260

ATTACACACA TCTGTCAGAG GTAGCTAGCG AAGGTGTCAC TGAAATATTT TTTGTTCCAG    1320

TTAGTATAAA TACGGAGGTA GAACAGCTCT CCGCGTGTAT ATCTTTTTTT GCGCTATACA    1380

AGAACAGGAA GAACGCATTT CCATACCTTT TTCTCCTTAC AGGTGCCCTC TGAGTAGTGT    1440

CACGAACGAG GAAAAAGATT AATATTACTG TTTTTATATT CAAAAAGAGT AAAGCCGTTG    1500

CTATATACGA AT                                                       1512
```

(2) INFORMATION FOR SEQ ID NO:5:

(i) SEQUENCE CHARACTERISTICS:
        (A) LENGTH: 29
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:5:

```
CTGGAAGCTT TCCAACCCTG CGCATTCAC                                       29
```

(2) INFORMATION FOR SEQ ID NO:6:

(i) SEQUENCE CHARACTERISTICS:
        (A) LENGTH: 25
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:6:

```
AACTGGATCC CCCACGGTAA TCGTC                                           25
```

(2) INFORMATION FOR SEQ ID NO:7:

(i) SEQUENCE CHARACTERISTICS:
        (A) LENGTH: 29
        (B) TYPE: nucleic acid
        (C) STRANDEDNESS: single
        (D) TOPOLOGY: linear     (ii) MOLECULE TYPE: other nucleic acid (synthetic DNA)

(xi) SEQUENCE DESCRIPTION: SEQ ID NO:7:

```
GGTACCCGGG AAAATGATTT CGAGAACAG                                       29
```

(2) INFORMATION FOR SEQ ID NO:8:

(i) SEQUENCE CHARACTERISTICS:
        (A) LENGTH: 926
        (B) TYPE: nucleic acid
        (C) STRANDEDNESS: double
        (D) TOPOLOGY: linear     (ii) MOLECULE TYPE: genomic DNA     (xi) SEQUENCE DESCRIPTION: SEQ ID NO:8:

-continued

```
TAATTTATAT TATTTGTTGC ATGATTTTTC TCTTTTATTT ATTTATATGT TGCCGATGGT    60

ACAAATTAGT ACTAGAAAAG AAAACCCACT ACTATGACTT GCAGAAAAAG TTATGTGTGC   120

CATAGATAGA TATAATTGCA TACCCACATC GTATACTCAA AATTCCGAAA AGAACATTTC   180

ATTTTTTATG AGGCAAACTG AACAACGCTT CGGTCCTTTT TTCATTCTAG AAATATATAT   240

TTATACATCA TTTTCAGAAG ATATTCAAAG AACTTATTGG GATGTCTATT TACTGAATAA   300

AGTATACACA AAAAACGAAT TTAAAATGGA AGGCATAAAT AGAAAACTTA GAAGTGAAAA   360

TCCTAAAACC GAAGGATATT TCAAATACGT AAAAGAAGTG AAAGATAAAA TAAAGCCCTA   420

AATAAGGAAG AAAAGAAGGG ATAACATTTT TTTTTGTTAC TTTTTGCTTA TTCCTCACCT   480

AAACAGAAGG AAAAAGCCAT TCTTGTTTAA AGAGTATTTT TAAAGCGTTC ATGAAAAGTC   540

ACAGTCCAAG GAGTATTTCA AATTGTCACT TGAAGTGAAA ACACCCCAGT GCTTCTCGAC   600

ATCAGAGGTA CCAGAGGTGT TTGGCTTCCA ATCTTCATCA AAGGCTTCAA AAACAATAAC   660

GTTAACACCC CAAGCTCTCA TGGAACAGAT ACCTTCTTTC CAGAATTGTT TGGCGTTGTC   720

AACAGATGGG TAAGAACTTT CAAAGTTGGT ACCATCAGTT GGCCAACCGG TCTCACCAAC   780

CCAGAAGGTA ATATCGGTAG AACCTTTAGT AGATTGGATA ACCTGTAGAG CTTGCATAAT   840

ATCATCAAAG AATGAGTAAG AGGCATTTTG CATGGTTTGA CCTTGCCAGT AGGAGAACGC   900

GTTAGCCATA ACAAAATCGG AAGCTT                                       926
```